United States Patent
Roznick et al.

(10) Patent No.: US 12,277,668 B2
(45) Date of Patent: Apr. 15, 2025

(54) DETERMINING VOLUME OF A SELECTABLE REGION USING EXTENDED REALITY

(71) Applicant: Intuitive Research and Technology Corporation, Huntsville, AL (US)

(72) Inventors: James S. Roznick, Huntsville, AL (US); Kyle Jordan Russell, Huntsville, AL (US)

(73) Assignee: INTUITIVE RESEARCH AND TECHNOLOGY CORPORATION, Huntsville, AL (US)

( * ) Notice: Subject to any disclaimer, the term of this patent is extended or adjusted under 35 U.S.C. 154(b) by 172 days.

(21) Appl. No.: 17/585,336

(22) Filed: Jan. 26, 2022

(65) Prior Publication Data
US 2023/0237612 A1    Jul. 27, 2023

(51) Int. Cl.
*G06T 3/18* (2024.01)
*G06F 3/01* (2006.01)
*G06T 7/00* (2017.01)
*G06T 19/00* (2011.01)
*G16H 30/40* (2018.01)

(52) U.S. Cl.
CPC ............... *G06T 3/18* (2024.01); *G06F 3/011* (2013.01); *G06T 7/0012* (2013.01); *G06T 19/003* (2013.01); *G16H 30/40* (2018.01); *G06T 2210/56* (2013.01)

(58) Field of Classification Search
CPC ... G06T 3/0093; G06T 7/0012; G06T 19/003; G06T 2210/56; G16H 30/40; G06F 3/011
See application file for complete search history.

(56) References Cited

U.S. PATENT DOCUMENTS

| | | | |
|---|---|---|---|
| 7,920,139 B2* | 4/2011 | Nystad | G06T 11/001 345/611 |
| 10,956,635 B1* | 3/2021 | Douglas | G06N 3/045 |
| 11,238,197 B1* | 2/2022 | Douglas | G16H 20/40 |
| 11,704,804 B2* | 7/2023 | Abrol | G06T 7/11 382/131 |
| 2009/0196342 A1* | 8/2009 | Divorra Escoda | H04N 19/50 375/E7.126 |
| 2014/0254861 A1* | 9/2014 | Nelson, Jr. | A01B 69/008 382/100 |
| 2015/0321694 A1* | 11/2015 | Nelson, Jr. | G06V 10/48 382/104 |
| 2020/0105070 A1* | 4/2020 | Coustaud | G06T 19/00 |
| 2020/0394848 A1* | 12/2020 | Choudhary | G06T 7/50 |
| 2021/0397876 A1* | 12/2021 | Hemani | G06V 10/761 |
| 2021/0401392 A1* | 12/2021 | Bengtsson | A61B 6/5217 |

(Continued)

*Primary Examiner* — Abderrahim Merouan
(74) *Attorney, Agent, or Firm* — Workman Nydegger

(57) ABSTRACT

A system for determining volume of a selectable region is configurable to (i) obtain user input directed to a 3D representation of a set of 2D images and (ii) based on the user input, selectively modify one or more mask pixels of one or more respective selection masks. Each 2D image of the set of 2D images is associated with a respective selection mask. The 3D representation represents pixels of the set of 2D images with corresponding voxels. The user input selects one or more voxels of the 3D representation. The one or more mask pixels is associated with one or more pixels of the set of 2D images that correspond to the one or more voxels of the 3D representation selected via the user input.

20 Claims, 12 Drawing Sheets

(56) References Cited

U.S. PATENT DOCUMENTS

| | | | |
|---|---|---|---|
| 2022/0028129 A1* | 1/2022 | Balashova | G06T 11/006 |
| 2022/0383585 A1* | 12/2022 | Lee | G06T 15/08 |
| 2023/0041575 A1* | 2/2023 | Tan | G06T 11/006 |

* cited by examiner

DETERMINING VOLUME OF A SELECTABLE REGION USING EXTENDED REALITY

BACKGROUND

Various medical imaging modalities exist, such as x-ray, computed tomography (CT), computed tomography perfusion (CTP) imaging, positron emission tomography (PET), single-photon emission computed tomography (SPECT), magnetic resonance imaging (MRI), ultrasound, and/or others. Many medical imaging modalities generate a set of images (referred to as "slices" or "image slices") that provides representations of structures within a patient's body. The slices of the set of images are typically associated with different positions along a patient's body. For example, where each image depicts a cross-section of the patient's body in the x-dimension and the y-dimension, each image may be associated with a different z-position (e.g., height). In this regard, a subset of contiguous image slices may provide contiguous representations of cross-sections of the patient's body. Structures of a patient's body may thus be depicted in multiple image slices.

Various analyses may be performed using sets of medical images. For example, measurements of structures depicted in the image slices may be obtained for various purposes (e.g., to detect progression or existence of disease, to detect response to treatment, etc.). By way of non-limiting example, measurements of masses present in a patient's body may be obtained at different timepoints to determine tumor progression or response to treatment. Various types of measurements may be used to assess structures present in medical imagery, such as length, area, volume, and/or others.

Conventional methods for obtaining volume measurements from medical imagery include identifying a subset of contiguous image slices that depict a bodily structure of interest and measuring the area of the structure within each of the contiguous image slices. For instance, a radiologist may trace the structure within each image slice to compute per-slice area measurements. The area measurements may then be combined to provide a volume measurement (e.g., based on known image characteristics, such as a real-world volume represented by each pixel of the image slices).

Such techniques for obtaining volume measurements are cumbersome, inefficient, and prone to user error. Accordingly, there exists a need for improved systems, methods, and techniques for measuring volume from imagery (e.g., cross-sectional imagery).

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

Disclosed embodiments include determining volume of a selectable region using extended reality. Some embodiments provide a method including various acts, and/or executable instructions that are executable to configure a system to perform various acts. The acts include (i) obtaining user input directed to a 3D representation of a set of 2D images and (ii) based on the user input, selectively modifying one or more mask pixels of one or more respective selection masks. Each 2D image of the set of 2D images is associated with a respective selection mask. The 3D representation represents pixels of the set of 2D images with corresponding voxels. The user input selects one or more voxels of the 3D representation. The one or more mask pixels is associated with one or more pixels of the set of 2D images that correspond to the one or more voxels of the 3D representation selected via the user input.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings in which.

DETAILED DESCRIPTION

Disclosed embodiments are directed to systems, methods, devices, and/or techniques for facilitating image analysis, such as by determining a volume (or other output metric) of a selectable region that spans multiple images within an image set.

For example, a system may receive user input directed to voxels of a 3D model that depicts a set of 2D images (e.g., image slices of a set of cross-sectional medical imagery). The user input may select voxels of the 3D model, which may facilitate selection of corresponding image pixels (or selection mask pixels) of individual images of the set of 2D images upon which the 3D model is based. The quantity and/or location of the image pixels (or selection mask pixels) that are selected based on the user input directed to the 3D model may be used to generate various useful output metrics, such as a volume of the selected region (e.g., where the pixels and/or voxels are correlated to real-world measurements).

One will appreciate, in view of the present disclosure, that the techniques discussed herein may facilitate numerous benefits relative to existing approaches for analyzing sets of 2D imagery. For example, in the context of 2D cross-sectional medical imagery, the disclosed techniques may allow users to select areas across multiple contiguous image slices at the same time to generate volume measurements based on the selected areas. Users may make such selections utilizing an intuitive depiction of the bodily structures of interest, and users may make modifications to selected regions/volumes in real-time (e.g., as will be described in more detail hereinafter, volume measurements may be obtained utilizing parallel processing of selection masks associated with image slices).

Accordingly, in some instances, the disclosed techniques may enable users/enterprises to avoid the inefficiencies, mundanity, and/or errors associated with user-driven manual selection of areas of interest in contiguous image slices for determining a volume of interest.

Having just described some of the various high-level features and benefits of the disclosed embodiments, attention will now be directed to FIGS. 1 through 7. These Figures illustrate various conceptual representations, architectures, methods, and supporting illustrations related to the disclosed embodiments.

Example Systems and Techniques for Facilitating Image Analysis

Figure 1:
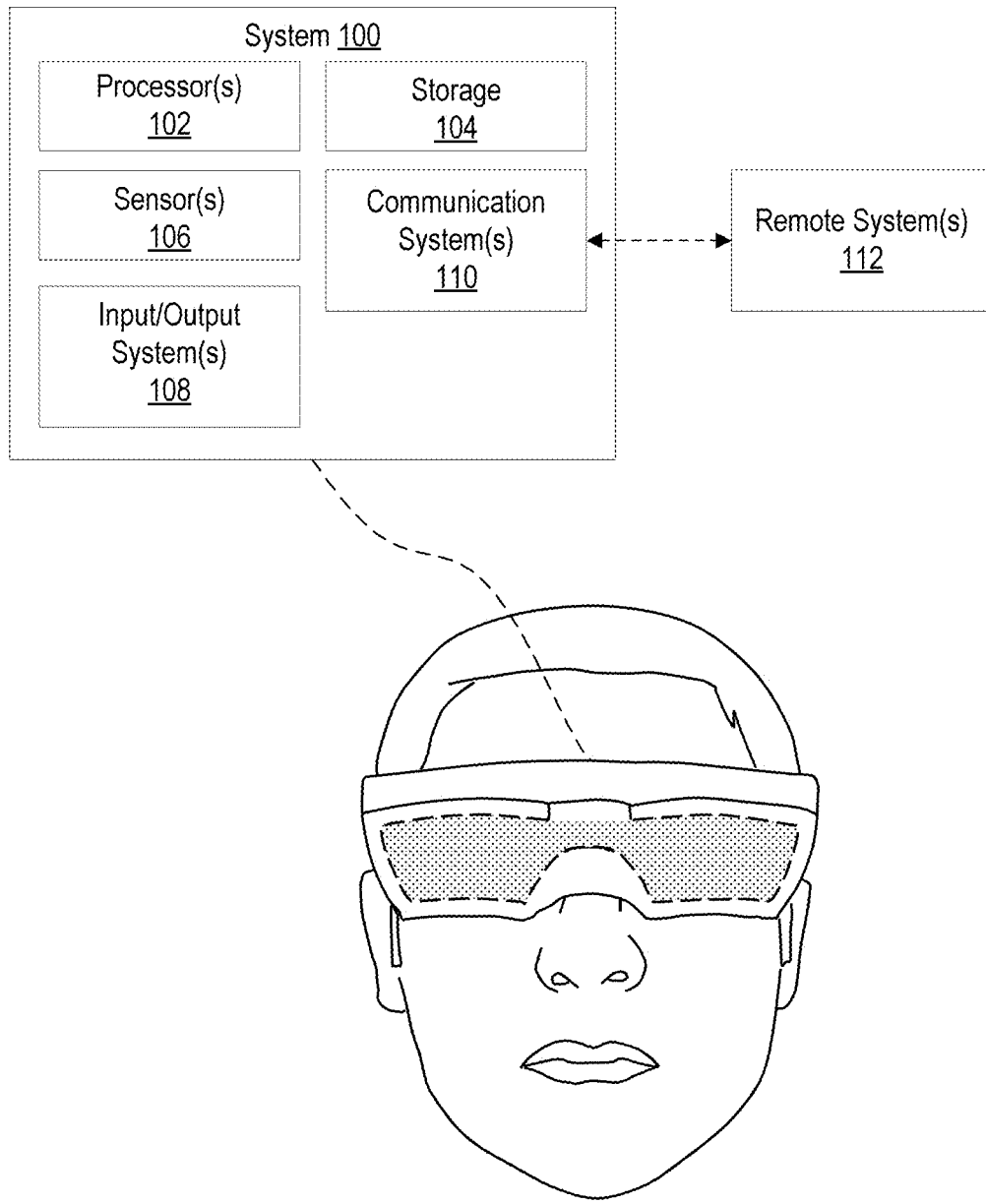
FIG. 1 illustrates example components of a system that may comprise or implement the disclosed embodiments.

Attention is now directed to FIG. 1, which illustrates an example system 100 that may include or be used to implement one or more disclosed embodiments. FIG. 1 depicts the system 100 as a head-mounted display (HMD) configured for placement over a head of a user to display virtual content for viewing by the user's eyes. Such an HMD may comprise a system configured to provide users with augmented reality (AR) experiences (e.g., with virtual content overlaid on a user's view of the real world), virtual reality (VR) experiences (e.g., immersive experiences where the user's view of the real world is obstructed), and/or any other type of extended reality (XR) experience. Although the present disclosure focuses, in at least some respects, on a system 100 implemented as an HMD, it should be noted that the techniques described herein may be implemented using other types of systems/devices, without limitation.

FIG. 1 illustrates various example components of the system 100. For example, FIG. 1 illustrates an implementation in which the system includes processor(s) 102, storage 104, sensor(s) 106, I/O system(s) 108, and communication system(s) 110. Although FIG. 1 illustrates a system 100 as including particular components, one will appreciate, in view of the present disclosure, that a system 100 may comprise any number of additional or alternative components.

The processor(s) 102 may comprise one or more sets of electronic circuitries that include any number of logic units, registers, and/or control units to facilitate the execution of computer-readable instructions (e.g., instructions that form a computer program). Such computer-readable instructions may be stored within storage 104. The storage 104 may comprise physical system memory and may be volatile, non-volatile, or some combination thereof. Furthermore, storage 104 may comprise local storage, remote storage (e.g., accessible via communication system(s) 110 or otherwise), or some combination thereof. Additional details related to processors (e.g., processor(s) 102) and computer storage media (e.g., storage 104) will be provided hereinafter.

In some implementations, the processor(s) 102 may comprise or be configurable to execute any combination of software and/or hardware components that are operable to facilitate processing using machine learning models or other artificial intelligence-based structures/architectures. For example, processor(s) 102 may comprise and/or utilize hardware components or computer-executable instructions operable to carry out function blocks and/or processing layers configured in the form of, by way of non-limiting example, single-layer neural networks, feed forward neural networks, radial basis function networks, deep feed-forward networks, recurrent neural networks, long-short term memory (LSTM) networks, gated recurrent units, autoencoder neural networks, variational autoencoders, denoising autoencoders, sparse autoencoders, Markov chains, Hopfield neural networks, Boltzmann machine networks, restricted Boltzmann machine networks, deep belief networks, deep convolutional networks (or convolutional neural networks), deconvolutional neural networks, deep convolutional inverse graphics networks, generative adversarial networks, liquid state machines, extreme learning machines, echo state networks, deep residual networks, Kohonen networks, support vector machines, neural Turing machines, and/or others.

As will be described in more detail, the processor(s) 102 may be configured to execute instructions stored within storage 104 to perform certain actions. The actions may rely at least in part on data stored on storage 104 in a volatile or non-volatile manner. In some instances, the actions may rely at least in part on communication system(s) 110 for receiving data from remote system(s) 112, which may include, for example, separate systems or computing devices, sensors, and/or others. The communications system(s) 110 may comprise any combination of software or hardware components that are operable to facilitate communication between on-system components/devices and/or with off-system components/devices. For example, the communications system(s) 110 may comprise ports, buses, or other physical connection apparatuses for communicating with other devices/components. Additionally, or alternatively, the communications system(s) 110 may comprise systems/components operable to communicate wirelessly with external systems and/or devices through any suitable communication channel(s), such as, by way of non-limiting example, Bluetooth, ultra-wideband, WLAN, infrared communication, and/or others.

FIG. 1 illustrates that a system 100 may comprise or be in communication with sensor(s) 106. Sensor(s) 106 may comprise any device for capturing or measuring data representative of perceivable phenomenon. By way of non-limiting example, the sensor(s) 106 may comprise one or more image sensors, microphones, thermometers, barometers, magnetometers, accelerometers, gyroscopes, and/or others. For example, the sensor(s) 106 may include inertial measurement unit(s) (IMU(s)), which may comprise any number of accelerometers, gyroscopes, and/or magnetometers to capture motion data associated with the system 100 as the system moves within physical space. The motion data may comprise or be used to generate pose data, which may describe the position and/or orientation (e.g., 6 degrees of freedom pose) and/or change of position (e.g., velocity and/or acceleration) and/or change of orientation (e.g., angular velocity and/or angular acceleration) of the system 100. The pose data may be used to facilitate XR experiences.

Furthermore, FIG. 1 illustrates that a system 100 may comprise or be in communication with I/O system(s) 108. I/O system(s) 108 may include any type of input or output device such as, by way of non-limiting example, a touch screen, a mouse, a keyboard, a controller, and/or others, without limitation. For example, the I/O system(s) 108 may include a display system that may comprise any number of display panels, optics, laser scanning display assemblies, and/or other components.

Figure 2A:
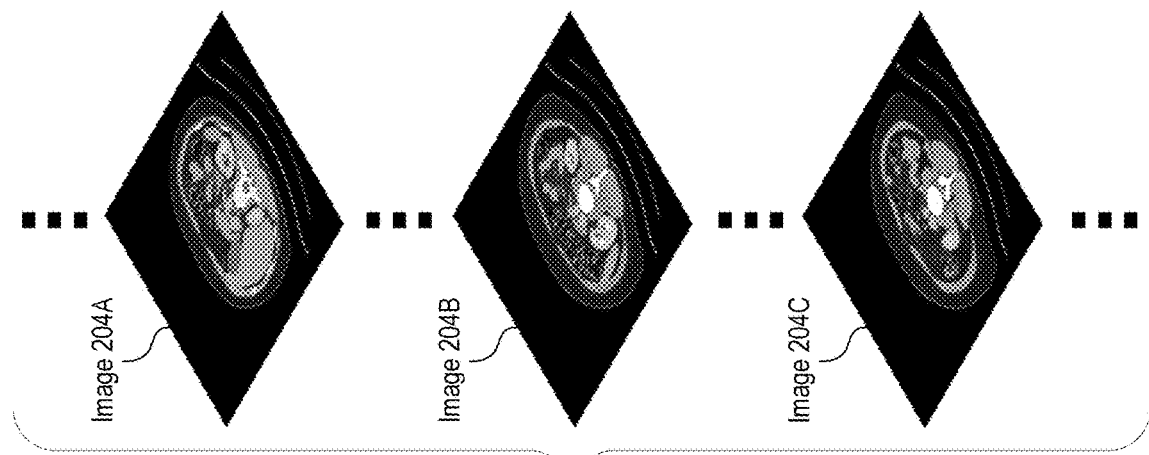
FIGS. 2A and 2B illustrate an example of presenting a 3D representation of a set of 2D images within a 3D environment.
Figure 2A:
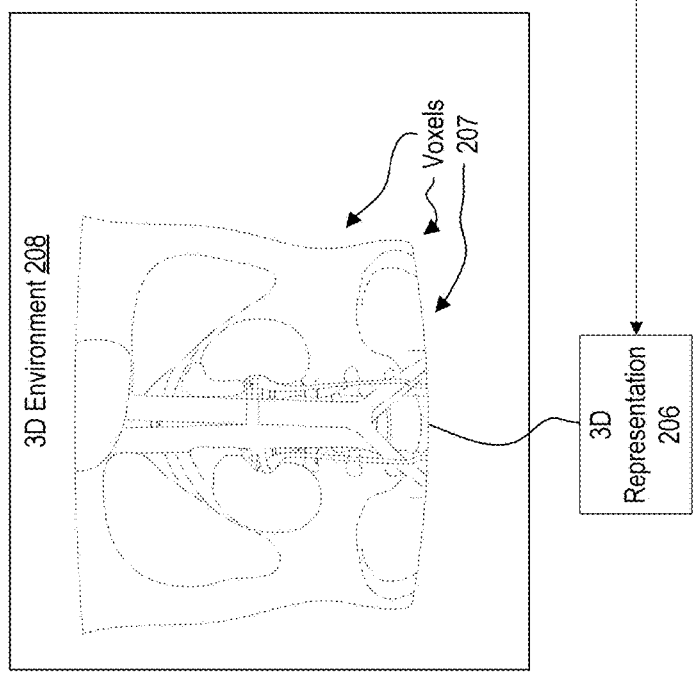
Figure 2B:
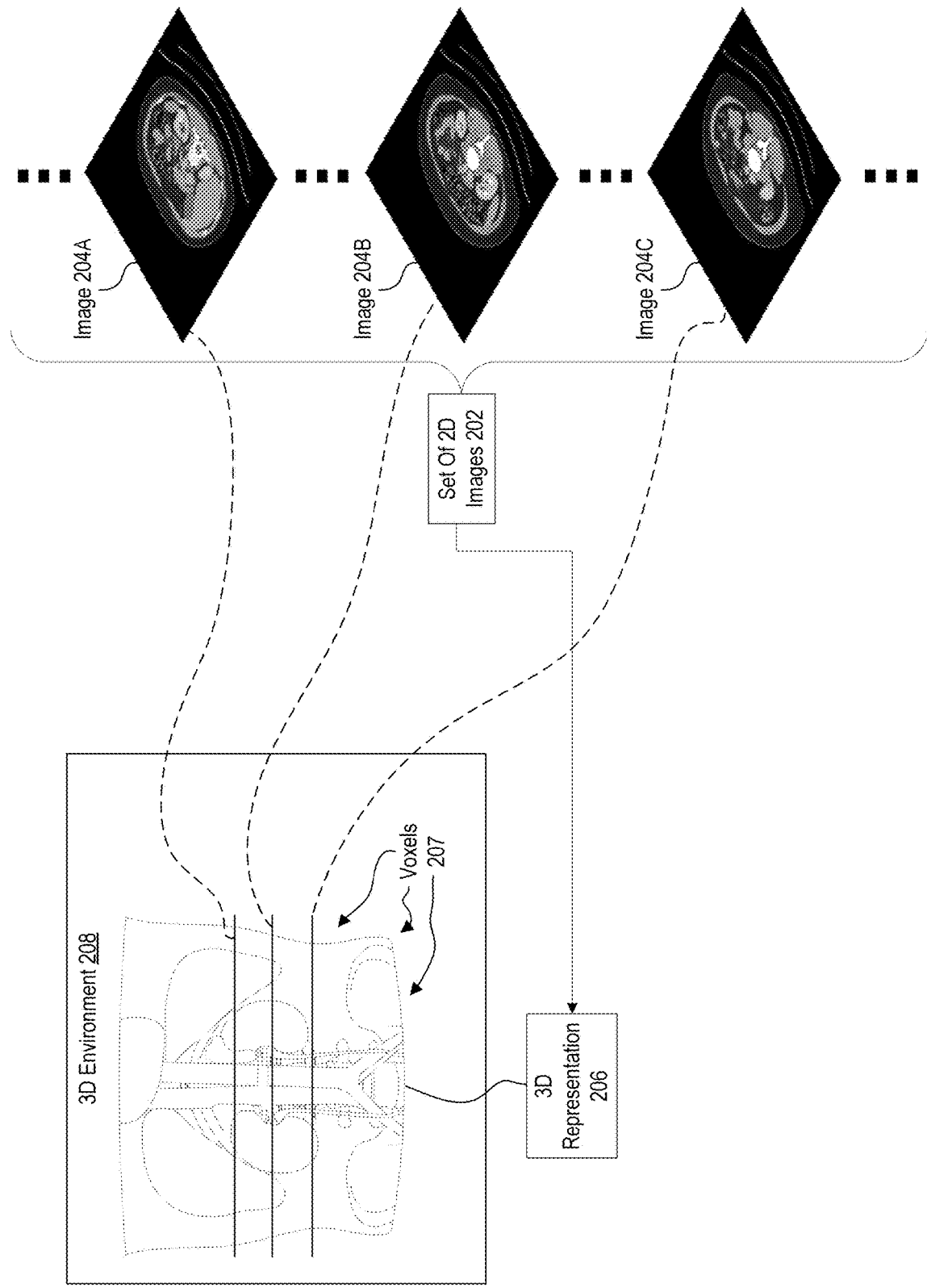

FIGS. 2A and 2B illustrate an example of presenting a 3D representation of a set of 2D images within a 3D environment. In particular, FIG. 2A illustrates a set of 2D images 202 and three example images thereof (i.e., image 204A, image 204B, and image 204C). The set of 2D images 202 may comprise any number of images, as indicated by the ellipses. Although the example of FIG. 2A depicts the images 204A, 204B, and 204C of the set of 2D images 202 as grayscale, cross-sectional medical images (e.g., CT images of an abdomen of a human patient), the principles discussed herein may be applied utilizing any type of 2D images.

FIG. 2A furthermore shows a 3D representation 206 presented within a 3D environment 208. The 3D environment 208 showing the 3D representation 206 may be presented/displayed on any suitable device, such as an extended reality (XR) head-mounted display (HMD) (e.g., system 100).

The 3D representation 206 may be generated based upon the set of 2D images 202, as indicated by the arrow extending from the set of 2D images 202 to the 3D representation 206 in FIG. 2A. For example, the voxels 207 of the 3D representation 206 may be generated based upon pixels of the images of the set of 2D images 202. For instance, FIG. 2B illustrates dashed lines extending from the images 204A, 204B, and 204C of the set of 2D images 202 toward different cross-sectional portions of the 3D representation 206, indicating that the voxels 207 forming the cross-sectional portions of the 3D representation 206 may be generated based upon the pixel values of image pixels of the 2D images 204A, 204B, and 204C. The 3D representation 206 may thus depict the various structures (e.g., human anatomical structures) represented in the set of 2D images 202 (e.g., the CT image set of the abdomen of the human patient), as shown in FIG. 2B. One will appreciate that interpolation and/or other processes may be performed to generate the voxels 207 based upon the pixels of the set of 2D images 202. Furthermore, although the 3D representation 206 is generated based upon the set of 2D images 202, it will be appreciated that the 3D representation 206 need not be generated directly from the raw images of the set of 2D images 202. For example, as will be discussed in more detail hereinafter, image data of a set of 2D images may be loaded into one or more channels of a multi-channel texture (e.g., a 4-channel red, green, blue, alpha (RGBA) texture), while other channels of the multi-channel texture may be utilized to store other information (e.g., pixel selection information of a selection mask, see FIGS. 3A and 3B). Accordingly, in some instances, a 3D representation may be generated based on a set of multi-channel textures, rather than the raw imagery.

Figure 2C:
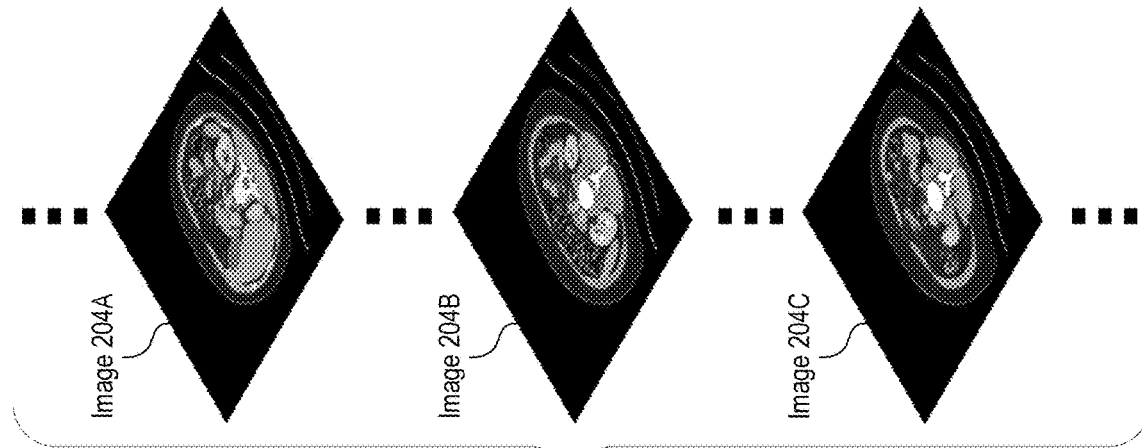
FIGS. 2C, 2D, and 2E illustrate examples of selection tools usable to select portions of the 3D representation of FIGS. 2A and 2B.
Figure 2C:
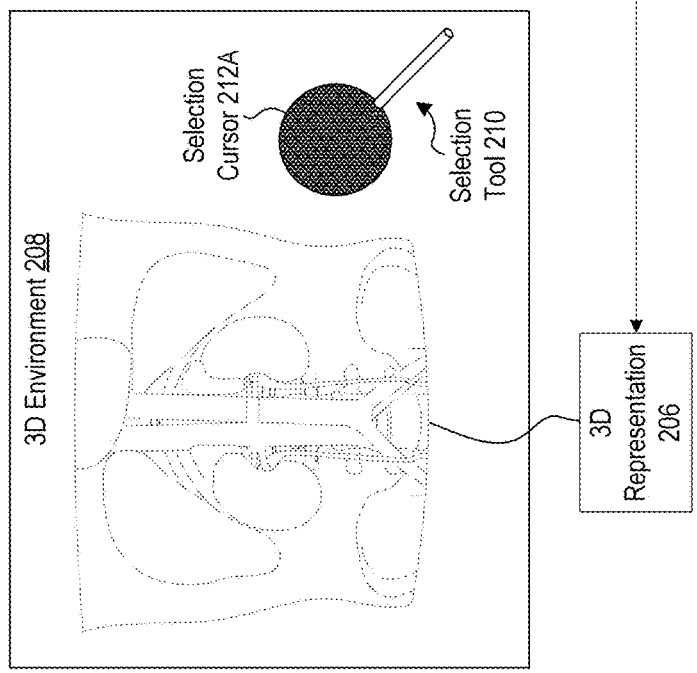
Figure 2D:
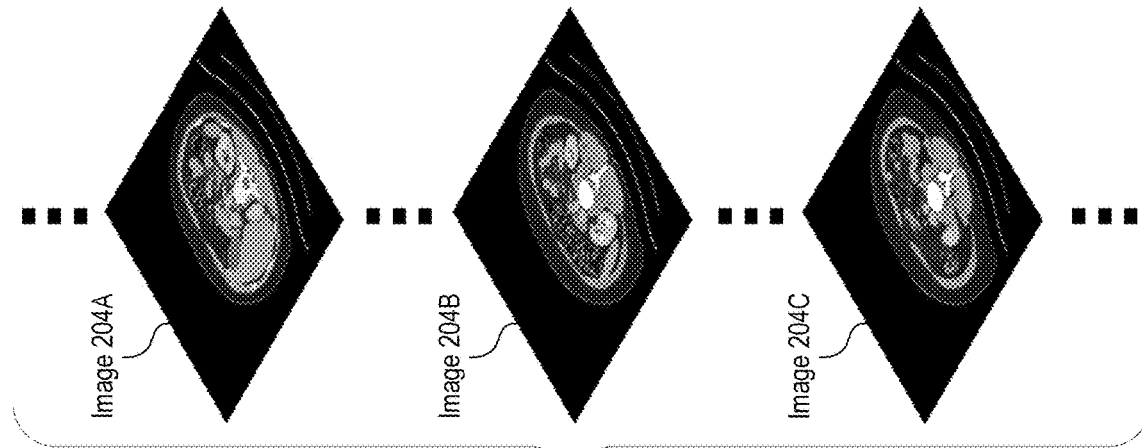
Figure 2D:
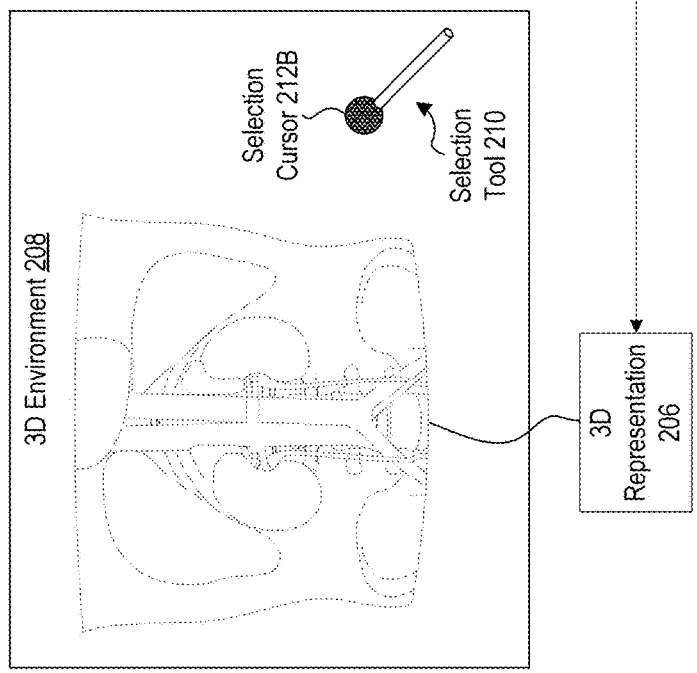
Figure 2E:
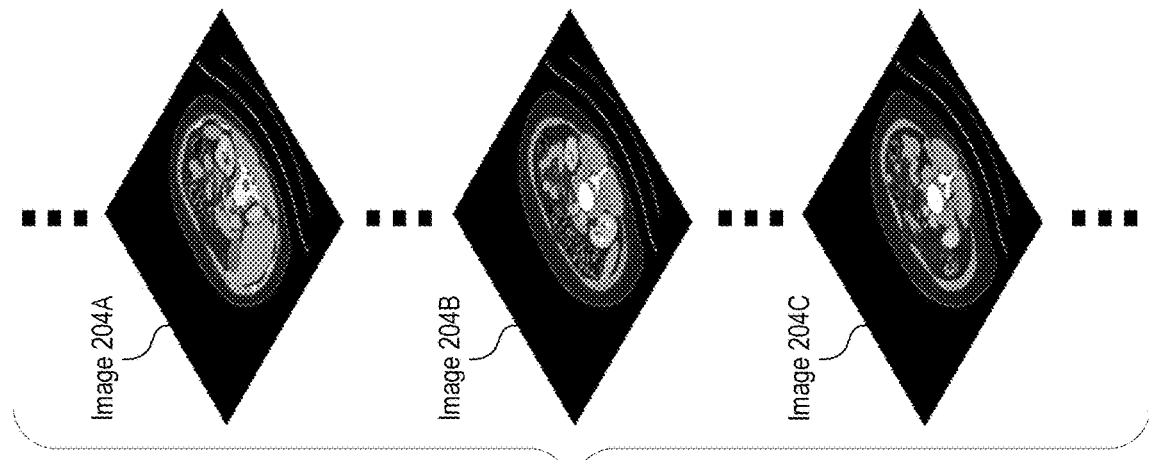
Figure 2E:
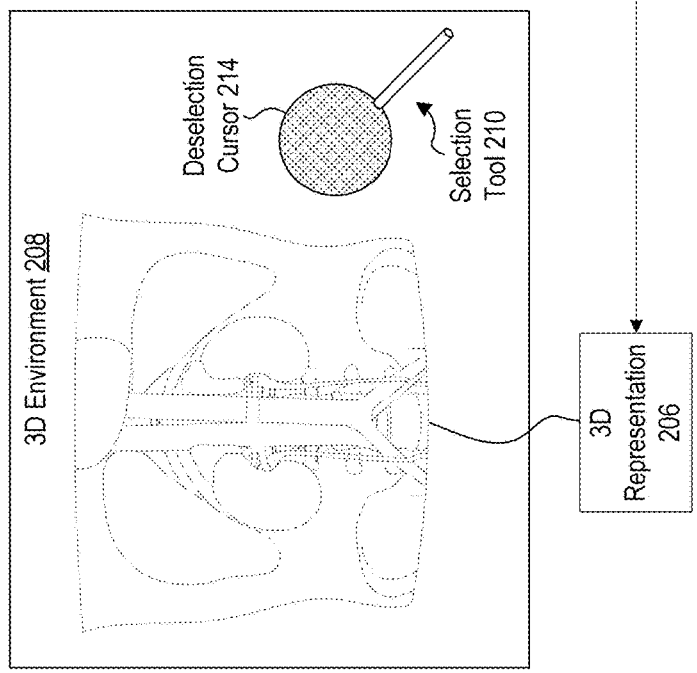

FIGS. 2C, 2D, and 2E illustrate examples of selection tools usable to select portions of the 3D representation 206 within the 3D environment 208. In particular, FIG. 2C illustrates a selection tool 210, which is depicted by way of example in the form of a control wand that is controllable by a user. For example, the positioning of the selection tool 210 within the 3D environment 208 may be determined based upon the relative or absolute position of a real-world object (e.g., a user's hand, a user's controller, etc.). By way of non-limiting example, an extended reality HMD may be associated with a handheld user controller, which the user may manipulate to facilitate desired positioning of the selection tool 210 within the 3D environment 208.

FIG. 2C illustrates a selection cursor 212A coupled to a portion (e.g., an end) of the selection tool 210, such that the position of the selection cursor 212A depends upon the position of the selection tool 210 (e.g., movement of the selection tool 210 causes movement of the selection cursor 212A). As will be described in more detail hereinafter, a user may utilize the selection tool 210 to position the selection cursor 212A to cause selection of one or more voxels of the 3D representation 206 (which, as noted above, are associated with corresponding pixels of the set of 2D images 202) to facilitate analysis of information represented within the set of 2D images 202.

In the example shown in FIG. 2C, the selection cursor 212A is provided in the form of a sphere, enabling the user to make spherical selections of voxels of the 3D representation 206. One will appreciate, in view of the present disclosure, that a selection cursor 212A and/or selection tool 210 may take on any suitable shape, size and/or format.

FIGS. 2D and 2E illustrate alternative forms of a selection cursor of a selection tool 210. In particular, FIG. 2D illustrates a selection cursor 212B with reduced size relative to the selection cursor 212A illustrated in FIG. 2C. In some instances, characteristics of the selection cursor are modifiable by a user (e.g., in real-time) to enable the user to make carefully-crafted selections of voxels of a 3D representation 206 (e.g., following the contours of structures or objects shown in the 3D representation 206).

FIG. 2E furthermore illustrates a deselection cursor 214, which may be usable to facilitate un-selection of voxels of the 3D representation 206 that were previously selected using the selection cursor 212A, 212B (or another form of selection cursor). Such functionality may further contribute to users' ability to make carefully-crafted selections of voxels of a 3D representation. For instance, a user may make a broad selection of voxels using a large selection cursor (e.g., selection cursor 212A), encompassing a structure of the 3D representation 206 that is of interest and voxels that lie outside of the structure of interest. For example, a user may make a sweeping motion with the selection tool 210, and positions of the selection tool 210 along the movement path may be interpolated to provide a smooth blend of selected voxels. The user may subsequently utilize a deselection cursor (e.g., deselection cursor 214) to unselect the voxels that lie outside of the structure of interest, such that only the voxels depicting the structure of interest remain selected.

Figure 3A:
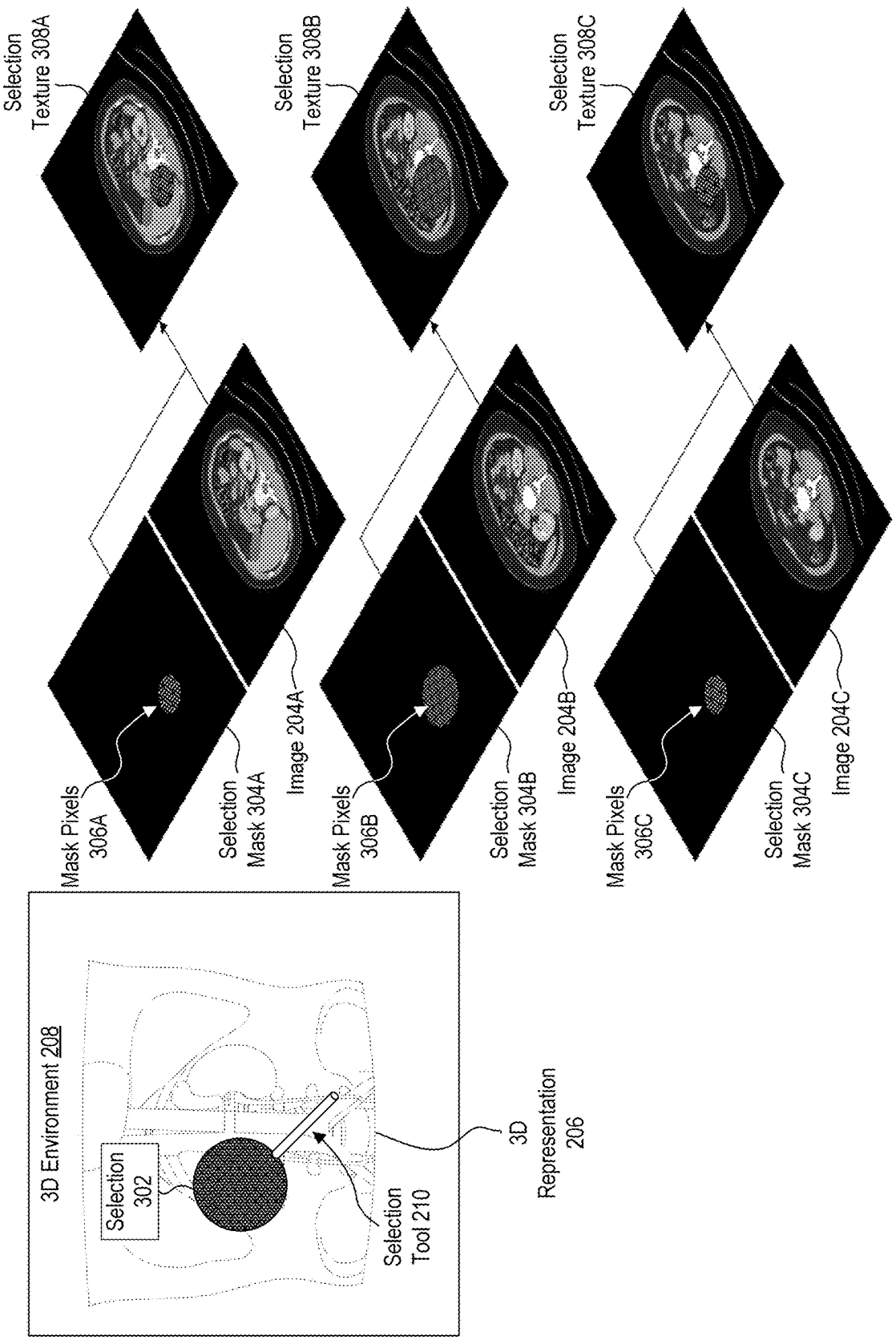
FIGS. 3A and 3B illustrate examples of utilizing a selection tool to select a region within the 3D representation of FIGS. 2A through 2E, corresponding to pixels within the set of 2D images of FIGS. 2A through 2E.
Figure 3B:
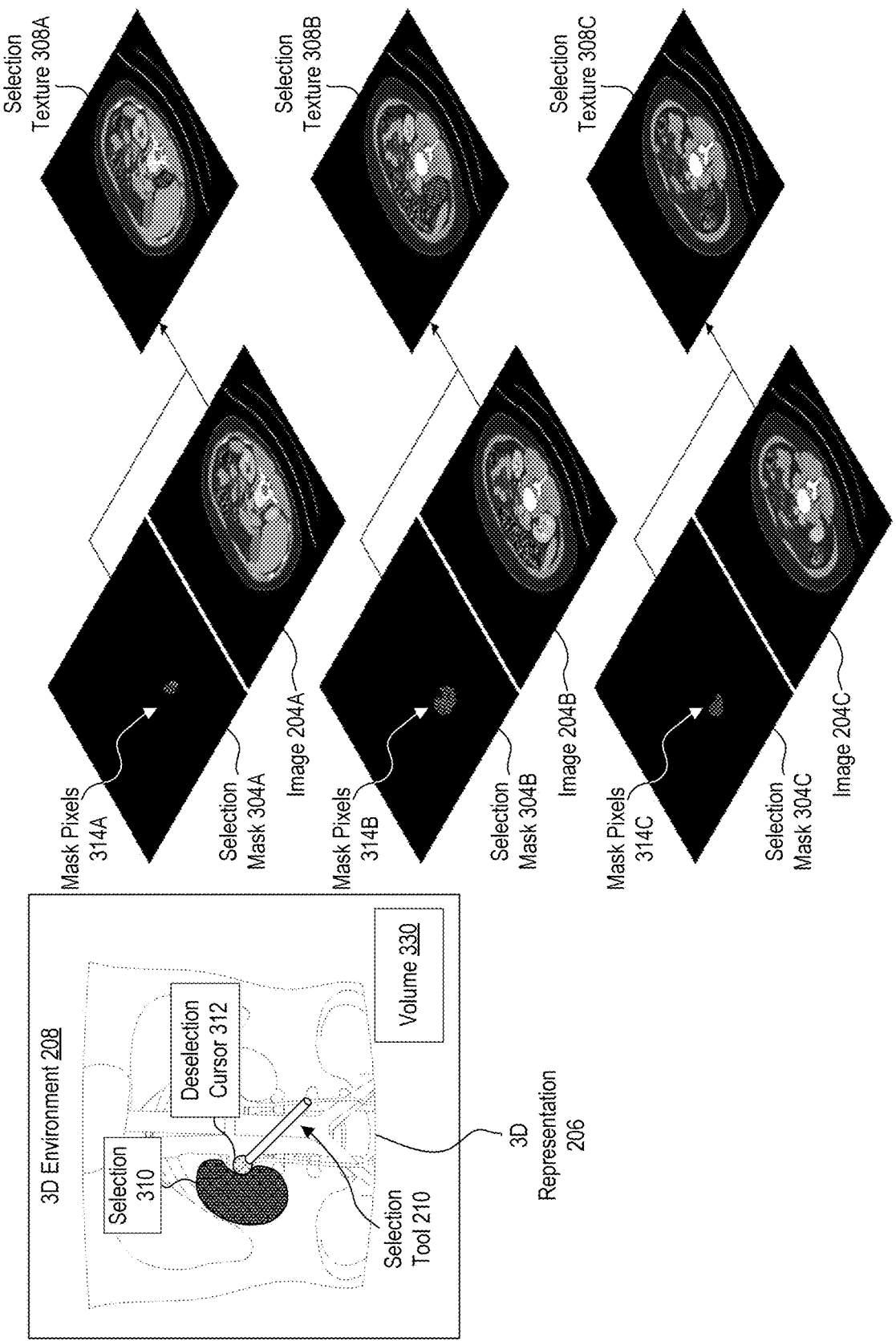

FIGS. 3A and 3B illustrate examples of user input utilizing a selection tool 210 to make a selection of voxels of the 3D representation 206 within the 3D environment 208. In particular, FIG. 3A illustrates a selection 302 of voxels of the 3D representation 206 obtained using the selection tool 210.

In the example of FIG. 3A, the selection 302 encompasses the volume of the right kidney of a patient depicted in the set of 2D images 202 and the 3D representation 206.

FIG. 3A furthermore illustrates selection masks associated with the various images of the set of 2D images upon which the 3D representation 206 is based. By way of illustrative example, FIG. 3A depicts a selection mask 304A associated with image 204A, a selection mask 304B associated with image 204B, and a selection mask 304C associated with image 204C. The selection masks and the images of the set of 2D images 202 may be associated with one another in various ways, without limitation. In some instances, each 2D image of the set of 2D images 202 (or image data thereof) and its respective selection mask are composited together as separate channels of a texture (e.g., as separate channels of an RGBA texture). For example, FIG. 3A depicts image 204A and selection mask 304A composited as selection texture 308A, image 204B and selection mask 304B composited as selection texture 308B, and image 204C and selection mask 304C composited as selection texture 308C. In some implementations, each image-mask texture for a set of 2D images (e.g., selection textures 308A, 308B, 308C, and/or others) may be combined in a composite texture.

FIG. 3A illustrates that the user input providing the selection 302 of voxels of the 3D representation 206 may cause mask pixels of one or more of the selection masks associated with a set of 2D images 202 to become modified (e.g., selected). As noted above, voxels of the 3D representation may be associated with corresponding image pixels of the set of 2D images 202. Accordingly, mask pixels of the selection masks that have pixel coordinates that match the image pixels of the set of 2D images 202 that correspond to the voxels of the selection 302 may be identified and selectively modified.

For example, FIG. 3A shows mask pixels 306A of selection mask 304A being modified to a selected state based upon the selected voxels of the selection 302 that lie on the cross-section of the 3D representation 206 attributable to image 204A. Similarly, FIG. 3A shows mask pixels 306B of selection mask 304B being modified to a selected state based upon the selected voxels of the selection 302 that lie on the cross-section of the 3D representation 206 attributable to image 204B, and FIG. 3A shows the mask pixels 306C of selection mask 304C being modified to a selected state based upon the selected voxels of the selection 302 that lie on the cross-section of the 3D representation 206 attributable to image 204C. As used herein, "mask pixels" may refer to components of a mask texture/image (e.g., a mask texture/image that is separate from a corresponding 2D image) or may refer to components of a mask channel (e.g., a mask channel that is composited with one or more image data channels of a texture, as discussed above).

As is evident from the selection textures 308A, 308B, and 308C shown in FIG. 3A, the mask pixels 306A, 306B, and 306C align with portions of the right kidney and surrounding structures that are shown in the associated images 204A, 204B, and 204C and that are encompassed by the selection 302 on the 3D representation 206.

FIG. 3A illustrates various mask pixels being modified to reflect selection based upon user input selecting voxels of the 3D representation 206. For instance, the mask pixels may comprise binary values, with a "0" indicating non-selection and with a "1" indicating selection, and user input providing the selection 302 of FIG. 3A may cause corresponding mask pixels to store values indicating selection (e.g., a "1"). For instance, the mask pixels 306A, 306B, and 306C of FIG. 3A may be regarded as storing a value indicating selection (e.g., a "1"), whereas mask pixels of the selection masks 304A, 304B, and 304C falling outside of the highlighted/emphasized regions of mask pixels 306A, 306B, and 306C may be regarded as storing values indicating non-selection (e.g., a "0").

Relatedly, user input directed to a portion of a 3D representation 206 may cause corresponding mask pixels to store values indicating deselection (e.g., a "0"). For example, FIG. 3B shows the selection tool 210 with a deselection cursor 312 directed to a portion of the 3D representation 206 surrounding a selection 310, indicating that a user provided user input via the deselection cursor 312 to unselect certain voxels to give the selection 310 its final shape/selection of voxels. For instance, starting with the selection 302 of FIG. 3A, a user may utilize the deselection cursor 312 to unselect portions of the selection 302 to arrive at the selection 310 of FIG. 3B.

In accordance with such a deselection, FIG. 3B illustrates each of the selection masks 304A, 304B, and 304C as comprising a different region of selected mask pixels 314A, 314B, and 314C, respectively, as compared to the regions of selected mask pixels 306A, 306B, and 306C of FIG. 3A. For example, the deselection of voxels brought about by use of the deselection cursor 312 may cause corresponding mask pixels of the selection masks 304A, 304B, and 304C that were previously in a selected state according to selection 302 of FIG. 3A to become deselected, resulting in the regions of selected mask pixels 314A, 314B, and 314C shown in FIG. 3B.

The selection functionality described above may allow users to intuitively and efficiently select relevant structures shown in a 3D representation (which is based upon 2D imagery). For example, the selection 310 of FIG. 3B obtained by user input focuses on the voxels depicting right kidney of the human patient depicted in the 3D representation 206. The mask pixels 314A, 314B, and 314C that become/remain selected based upon the selection 310 correspondingly focus on the right kidney as represented in the set of 2D images 202.

Additional or alternative techniques may be utilized to facilitate selection of 2D image pixels (e.g., mask pixels or image pixels) of a set of images based on a selection of voxels of a 3D representation based upon the set of images, in accordance with the present disclosure. For example, a user may direct a selection or deselection cursor within a 3D environment toward one or more voxels depicting a portion of a structure of interest of a 3D representation. The target voxel(s) are associated with one or more 2D image pixels and/or mask pixels of a set of 2D imagery (upon which the 3D representation is based). One or more segmentation operations (e.g., utilizing thresholding, clustering, edge detection, region-growing, and/or other segmentation techniques) may be performed on 2D images that include the 2D image pixels associated with the target voxels to identify a structure within the 2D images that encompasses the 2D image pixels associated with the target voxels. Mask pixels with coordinates that fall within the identified structure may then be automatically modified (e.g., to reflect selection or un-selection).

In some instances, 2D images may comprise pixels that do not represent relevant structures and are therefore not desirable candidates for selection according to the techniques discussed above. For example, many cross-sectional medical images capture air surrounding the patient's body, which is usually depicted by image pixels that have a zero or low intensity value. Accordingly, in some embodiments, one or more rules may be implemented to prevent selection of mask pixels associated with image pixels that fail to satisfy one or more conditions, such as an intensity threshold. Another example condition may comprise being bounded by pixels that satisfy an intensity threshold. Such conditions may allow selection of pixels representing air within a patient's lungs but may prevent selection of pixels representing air outside of a patient's body.

In some instances, mask pixels that store a value indicating selection (e.g., a "1") may be utilized to generate or calculate one or more output metrics usable to analyze one or more structures or aspects of the set of 2D images 202 that forms the basis of the 3D representation 206.

Figure 4:
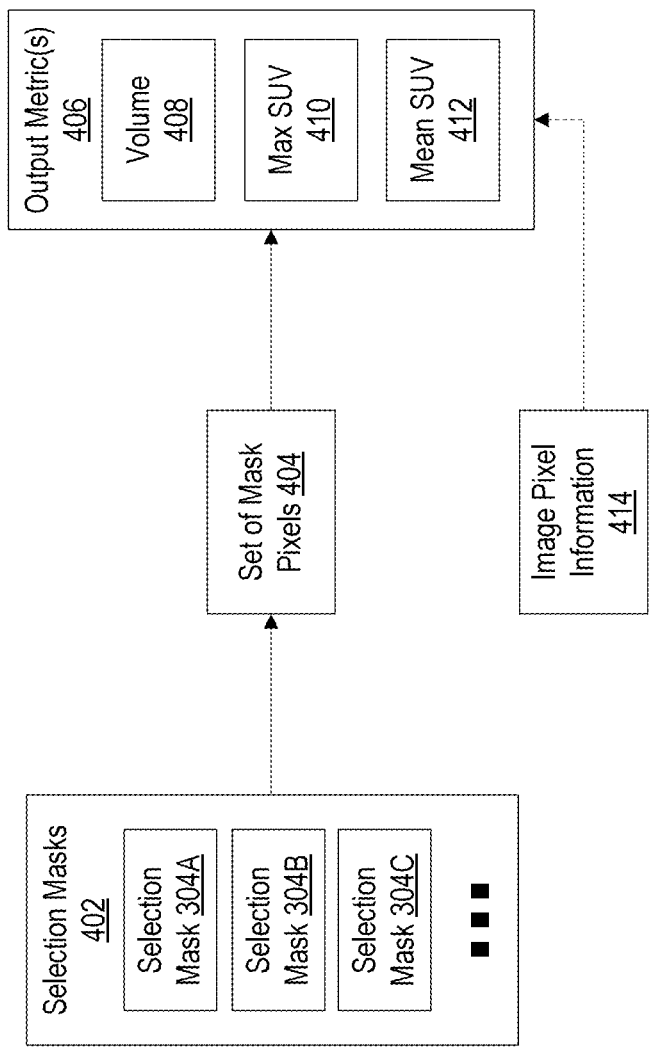
FIG. 4 illustrates a conceptual representation of generating output metrics based upon selected pixels from a set of 2D images.

FIG. 4 illustrates a conceptual representation of generating output metrics based upon selected pixels from a set of 2D images. In particular, FIG. 4 depicts selection masks 402, which may comprise each selection mask associated with a set of 2D images. Continuing with the examples of FIGS. 2A through 3B, the selection masks 402 of FIG. 4 include selection masks 304A, 304B, and 304C associated with images of the set of 2D images 202. The ellipsis indicates that the selection masks 402 may comprise any number of selection masks.

From the selection masks 402, mask pixels that store a value indicating selection may be identified, as represented in FIG. 4 by the set of mask pixels 404 derived from the selection masks 402. Based on the quantity of mask pixels within the set of mask pixels 404, and/or other aspects of the set of mask pixels 404 (e.g., pixel location, data associated with corresponding image pixels), output metric(s) 406 may be determined that may be usable for analyzing structures and/or aspects of the 2D images associated with the selection masks 402. Output metric(s) 406 may comprise a volume 408. For instance, in the context of medical imagery, each pixel of a cross-sectional image may be associated with a real-world unit volume. This unit volume may be multiplied by the quantity of mask pixels within the set of mask pixels 404 to provide a volume 408 of a region selected in a 3D representation (e.g., providing a volume for the selection 310 of the 3D representation 206 of FIG. 3B).

Other output metrics are within the scope of the present disclosure. For example, FIG. 4 illustrates a max SUV value 410 and a mean SUV value 412 that may be computed based on the set of mask pixels 404 and image pixel information 414. For example, positron emission tomography (PET) scans may include standardized uptake value (SUV) information associated with one or more regions thereof, which may be utilized to assess malignancy of lesions/tumors. Thus, based on the locations of the selected mask pixels of the set of mask pixels 404, image pixel information 414 including SUV information for image pixels at the same pixel locations as the selected mask pixels may be accessed and analyzed to determine a max SUV 410 and/or a mean SUV value 412. Other types of output metrics are within the scope of the present disclosure.

Output metrics may be dynamically measured for selected regions within a 3D environment 208 in real-time (or near real-time). In some instances, output metrics are displayed within a 3D environment contemporaneous with the selection that selects the voxels used to determine the output metric. For example, referring briefly to FIG. 3B, a volume 330 is displayed within the 3D environment 208 contemporaneous with the selection 310 of voxels for which the volume 330 is calculated (e.g., the voxels that correspond to image and/or mask pixels that store a value indicating selection). The volume 330 is also displayed contemporaneous with the 3D representation 206, which may provide users with an intuition of scale.

Figure 5:
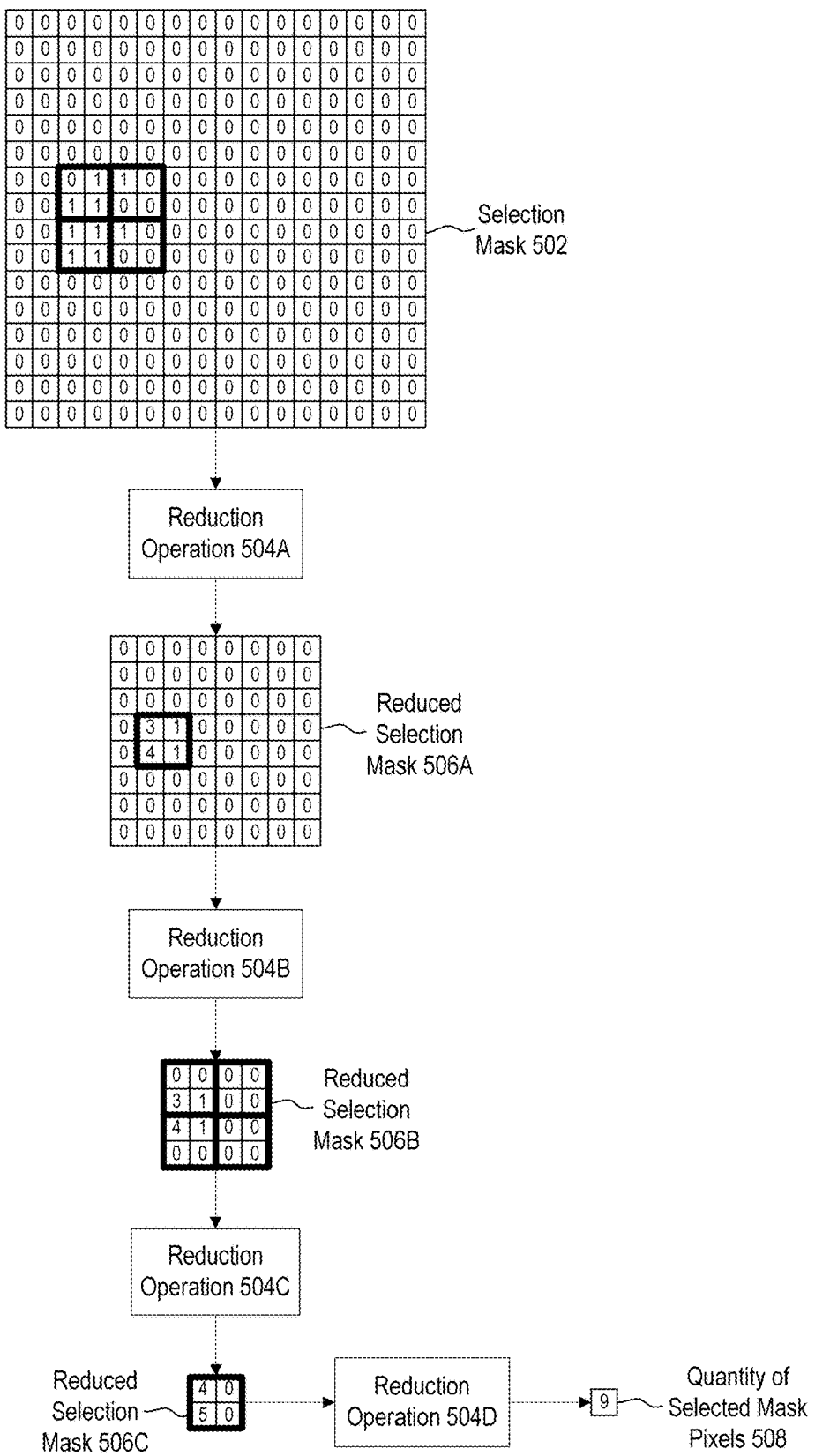
FIG. 5 illustrates a conceptual representation of determining a quantity of selected pixels associated with a 2D image.

As indicated above, such as where the output metric comprises a volume, the output metric may be determined based on the sum or quantity of selected mask pixels included in each of the selection masks. In some instances, processing is performed on the different selection masks 402 in parallel to facilitate rapid and/or efficient identification of the set of mask pixels 404 (e.g., the sum of mask pixels from each of the selection masks 402) and/or the output metric(s) 406. Such processing may be performed, in some instances, utilizing a shader of a graphics processing unit (GPU). FIG. 5 illustrates a conceptual representation of determining a quantity of selected mask pixels 508 from a selection mask 502. Such operations may be performed for each of the selection masks 402 of FIG. 4 (e.g., in parallel utilizing a shader of a GPU), and the quantities of selected mask pixels from all selection masks 402 may be combined to provide the set of mask pixels 404.

FIG. 5 conceptualizes a selection mask 502 that includes mask pixels storing a value of either "0" (indicating non-selection) or "1" (indicating selection). Pursuant to determining a quantity of selected mask pixels 508, a reduction operation 504A may be performed on the selection mask 502. A reduction operation 504A may include generating a reduced selection mask 506A, where each pixel of the reduced selection mask 506A is generated based upon a respective sum of pixels within a respective region of the selection mask 502. For example, FIG. 5 illustrates four 2×2 pixel regions in the selection mask 502 (with bolded lines). The mask pixel values within each of these 2×2 pixel regions may be separately summed to provide pixel values for separate pixels within the reduced selection mask 506A (i.e., the pixels within the bolded box of the reduced selection mask 506A). For example, the upper-left 2×2 box within the bolded lines of the selection mask 502 includes mask pixels having values of "0", "1", "1", and "1". Accordingly, the upper-left pixel within the bolded lines of the reduced selection mask 506A has a value of 3 (i.e., the sum of 0+1+1+1).

Although a 2×2 pixel region size is used in the example reduction operation 504A of FIG. 5, other pixel region sizes (or multiple pixel region sizes) may be utilized in accordance with the present disclosure.

As is evident from FIG. 5, the reduced selection mask 506A comprises a smaller pixel resolution than the selection mask 502. As is furthermore evident from FIG. 5, whereas the selection mask 502 comprises binary pixel values (which may be represented by a single 8-bit channel of a texture), the reduced selection mask 506A comprises integer pixel values (32-bit information). Accordingly, the reduction operation 504A may comprise generating a reduced selection mask 506A with higher-bit data than the input selection mask 502.

FIG. 5 illustrates that, in some implementations, multiple reduction operations may be performed to determine a quantity of selected mask pixels in an efficient manner. FIG. 5 illustrates the reduced selection mask 506A utilized as input to reduction operation 504B, which may generate pixels of a reduced selection mask 506B based on the sums of pixel regions within the input reduced selection mask 506A (e.g., 2×2 pixel regions, similar to the reduction operation 504A). The pixel resolution of reduced selection mask 506B is further reduced relative to selection mask 506A. One will appreciate, in view of the present disclosure, that different reduction operations may utilize different pixel region sizes to generate respective sums of pixel regions for obtaining output pixel values.

FIG. 5 similarly illustrates reduction operation 504C performed using reduced selection mask 506B as an input to generate reduced selection mask 506C (with a further reduced pixel resolution). The reduced selection mask 506C has a pixel resolution that corresponds to a pixel region size usable for determining a sum for an output pixel of a further reduced selection mask (e.g., a 2×2 pixel resolution). FIG. 5 illustrates reduction operation 504D, which utilizes reduced selection mask 506C to determine a quantity of selected mask pixels 508 (e.g., 9 in the example shown). The final sum represented by the quantity of selected mask pixels 508 represents the sum of selected mask pixels originally represented in the original selection mask 502.

Although four reduction operations are used in the example of FIG. 5, any number of reduction operations (e.g., one or more) may be performed to determine a quantity of selected mask pixels in accordance with the present disclosure.

In some instances, performing multiple iterative reduction operations may facilitate efficient and/or rapid determination of quantities of selected mask pixels for selection masks. Such operations may be performed in parallel for different selection masks, and the quantities of selected mask pixels from the different selection masks may be aggregated to determine a total quantity of selected mask pixels included for an entire set of 2D images. The total quantity may be used to determine one or more output metrics, such as volume (e.g., by multiplying the total quantity of selected mask pixels by a real-world unit volume associated with a pixel of the 2D images).

Although the present disclosure focuses, in at least some respects, on implementations in which a set of 2D images is used to generate a 3D representation, and user input directed to the 3D representation causes selection of mask pixels associated with the 2D images, the principles discussed herein may be applied in other contexts, such as volume sculpting. For example, a 3D representation or region within a 3D environment may be associated with a set of selection masks (e.g., without other image data accompanying the selection masks). The selection masks may be associated with respective layers of the 3D representation, with voxels of the various layers of the 3D representation corresponding to mask pixels of the selection masks. User input may be directed to voxels of the 3D representation, and mask pixels of the selection masks may be modified based upon the user input. The selected mask pixels within the set of selection masks may accordingly represent the shape, size, and/or other aspects of the selected voxels of the 3D representation. The selected mask pixels may be utilized to generate various metrics (e.g., volume).

Example Method(s) for Facilitating Image Analysis

The following discussion now refers to a number of methods and method acts that may be performed. Although the method acts may be discussed in a certain order or illustrated in a flow chart as occurring in a particular order, no particular ordering is required unless specifically stated, or required because an act is dependent on another act being completed prior to the act being performed.

Figure 6:
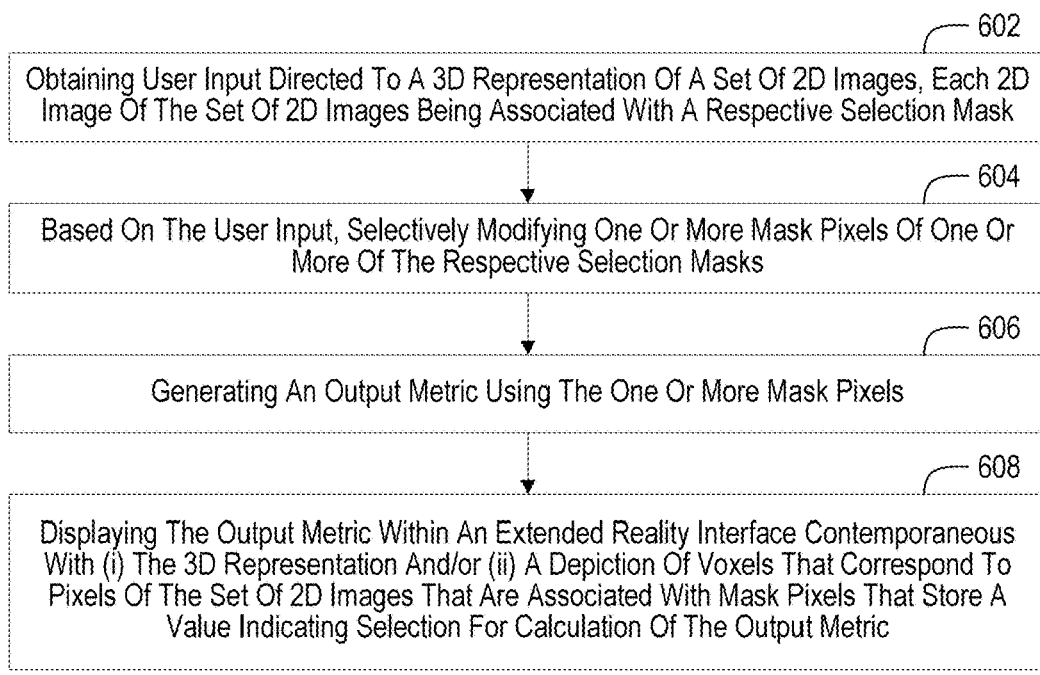
FIG. 6 illustrates a flow diagram depicting acts associated with facilitating image analysis, in accordance with implementations of the present disclosure.

FIG. 6 illustrates a flow diagram 600 depicting acts associated with facilitating image analysis, in accordance with implementations of the present disclosure. The discussion of the various acts of flow diagram 600 refers to the various hardware elements discussed herein with reference to FIG. 1.

Act 602 of flow diagram 600 includes obtaining user input directed to a 3D representation of a set of 2D images, each 2D image of the set of 2D images being associated with a respective selection mask. Act 602 is performed, in some instances, utilizing processor(s) 102, storage 104, sensor(s) 106, input/output system(s) 108, communication system(s) 110, and/or other components of a system 100 (e.g., an XR HMD).

The 3D representation may represent pixels of the set of 2D images with corresponding voxels. The user input may select one or more voxels of the 3D representation. The set of 2D images may comprise a set of grayscale images, a set of cross-sectional medical images, or other types of images. In some instances, the 3D representation is displayed on an XR device, and/or the user input is received via the XR device. In some instances, for each 2D image of the set of 2D images, the 2D image and the respective selection mask are composited as separate channels of a respective texture.

Act 604 of flow diagram 600 includes, based on the user input, selectively modifying one or more mask pixels of one or more of the respective selection masks. Act 604 is performed, in some instances, utilizing processor(s) 102, storage 104, sensor(s) 106, input/output system(s) 108, communication system(s) 110, and/or other components of a system 100 (e.g., an HMD).

The one or more mask pixels may be associated with one or more pixels of the set of 2D images that correspond to the one or more voxels of the 3D representation selected via the user input. In some instances, selectively modifying the one or more mask pixels causes the one or more mask pixels to store a value indicating selection for a calculation of an output metric. In some instances, selectively modifying the one or more mask pixels causes the one or more mask pixels to store a value indicating deselection of the one or more mask pixels or data associated therewith for a calculation of an output metric.

Act 606 of flow diagram 600 includes generating an output metric using the one or more mask pixels. Act 606 is performed, in some instances, utilizing processor(s) 102, storage 104, sensor(s) 106, input/output system(s) 108, communication system(s) 110, and/or other components of a system 100 (e.g., an HMD).

In some instances, generating the output metric is performed utilizing a shader of a graphics processing unit. In some instances, generating the output metric may include determining a set of mask pixels within the one or more of the respective selection masks that store the value indicating selection for the calculation of the output metric. In some instances, determining the set of mask pixels within the one or more of the respective selection masks that store the value indicating selection for the calculation of the output metric comprises, for each respective selection mask of the one or more of the respective selection masks, performing a reduction operation. The reduction operation may comprise, for each pixel region of a plurality of pixel regions of the respective selection mask, determining a respective sum of mask pixels within the pixel region. The reduction operation may comprise, for each respective selection mask of the one or more respective selection masks, outputting the respective sums of mask pixels as a reduced mask. Each of the respective sums may be represented as a corresponding pixel of the reduced mask. The reduced mask may comprise a lower resolution than the respective selection mask. The reduced mask may comprise higher-bit data than the respective selection mask. Determining the set of mask pixels within the one or more of the respective selection masks that store the value indicating selection for the calculation of the output metric may further comprise performing one or more additional reduction operations based on output of the reduction operation or a preceding reduction operation. The one or more additional reduction operations may comprise determining sums of regions of input pixels. The set of mask pixels may be based upon each of the respective sums. The output metric may be determined using the set of mask pixels. The output metric may comprise a volume.

Act 608 of flow diagram 600 includes displaying the output metric within an extended reality interface contemporaneous with (i) the 3D representation and/or (ii) a depiction of voxels that correspond to pixels of the set of 2D images that are associated with mask pixels that store a value indicating selection for calculation of the output metric. Act 608 is performed, in some instances, utilizing processor(s) 102, storage 104, sensor(s) 106, input/output system(s) 108, communication system(s) 110, and/or other components of a system 100 (e.g., an HMD).

Example Computer/Computer Systems

Figure 7:
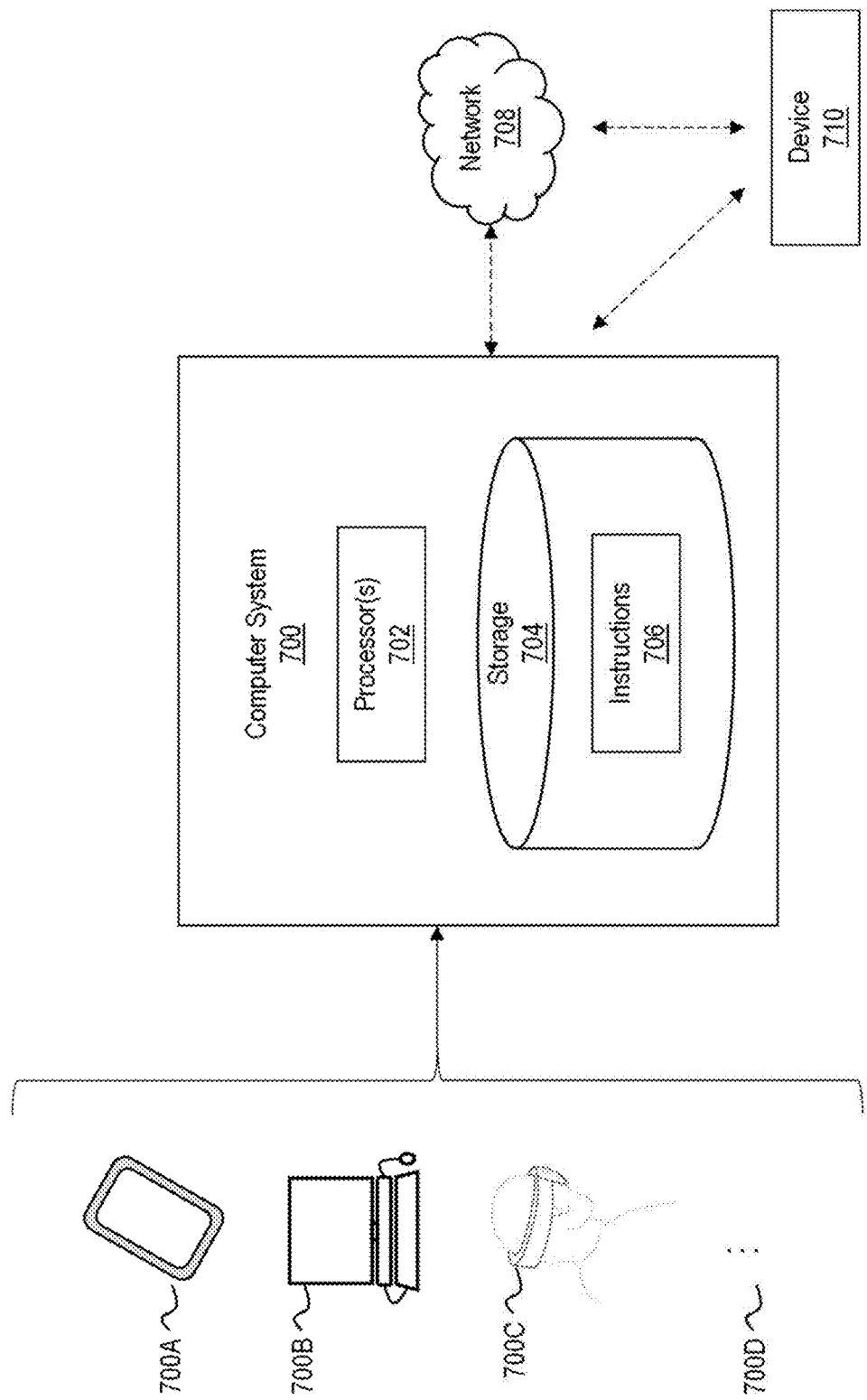
FIG. 7 illustrates example components of computer systems that may comprise or implement one or more disclosed embodiments.

Attention will now be directed to FIG. 7 which illustrates an example computer system 700 that may include and/or be used to perform any of the operations described herein. Computer system 700 may take various different forms. For example, computer system 700 may be embodied as a tablet, a desktop, a laptop, a mobile device, or a standalone device, such as those described throughout this disclosure. Computer system 700 may also be a distributed system that includes one or more connected computing components/devices that are in communication with computer system 700.

In its most basic configuration, computer system 700 includes various different components. FIG. 7 shows that computer system 700 includes one or more processor(s) 702 (aka a "hardware processing unit") and storage 704.

Regarding the processor(s) 702, it will be appreciated that the functionality described herein can be performed, at least in part, by one or more hardware logic components (e.g., the processor(s) 702). For example, and without limitation, illustrative types of hardware logic components/processors that can be used include Field-Programmable Gate Arrays ("FPGA"), Program-Specific or Application-Specific Integrated Circuits ("ASIC"), Program-Specific Standard Products ("ASSP"), System-On-A-Chip Systems ("SOC"), Complex Programmable Logic Devices ("CPLD"), Central Processing Units ("CPU"), Graphical Processing Units ("GPU"), or any other type of programmable hardware.

As used herein, the terms "executable module," "executable component," "component," "module," or "engine" can refer to hardware processing units or to software objects, routines, or methods that may be executed on computer system 700. The different components, modules, engines, and services described herein may be implemented as objects or processors that execute on computer system 700 (e.g. as separate threads).

Storage 704 may be physical system memory, which may be volatile, non-volatile, or some combination of the two. The term "memory" may also be used herein to refer to non-volatile mass storage such as physical storage media. If computer system 700 is distributed, the processing, memory, and/or storage capability may be distributed as well.

Storage 704 is shown as including executable instructions 706. The executable instructions 706 represent instructions that are executable by the processor(s) 702 of computer system 700 to perform the disclosed operations, such as those described in the various methods.

The disclosed embodiments may comprise or utilize a special-purpose or general-purpose computer including computer hardware, such as, for example, one or more processors (such as processor(s) 702) and system memory (such as storage 704), as discussed in greater detail below. Embodiments also include physical and other computer-readable media for carrying or storing computer-executable instructions and/or data structures. Such computer-readable media can be any available media that can be accessed by a general-purpose or special-purpose computer system. Computer-readable media that store computer-executable instructions in the form of data are "physical computer storage media" or a "hardware storage device." Furthermore, computer-readable storage media, which includes physical computer storage media and hardware storage devices, exclude signals, carrier waves, and propagating signals. On the other hand, computer-readable media that carry computer-executable instructions are "transmission media" and include signals, carrier waves, and propagating signals. Thus, by way of example and not limitation, the current embodiments can comprise at least two distinctly different kinds of computer-readable media: computer storage media and transmission media.

Computer storage media (aka "hardware storage device") are computer-readable hardware storage devices, such as RAM, ROM, EEPROM, CD-ROM, solid state drives ("SSD") that are based on RAM, Flash memory, phase-change memory ("PCM"), or other types of memory, or other optical disk storage, magnetic disk storage or other magnetic storage devices, or any other medium that can be used to store desired program code means in the form of computer-executable instructions, data, or data structures and that can be accessed by a general-purpose or special-purpose computer.

Computer system 700 may also be connected (via a wired or wireless connection) to external sensors (e.g., one or more remote cameras) or devices via a network 708. For example, computer system 700 can communicate with any number devices (e.g., device 710) or cloud services to obtain or process data. In some cases, network 708 may itself be a cloud network. Furthermore, computer system 700 may also be connected through one or more wired or wireless networks 708 to remote/separate computer systems(s) that are configured to perform any of the processing described with regard to computer system 700.

A "network," like network 708, is defined as one or more data links and/or data switches that enable the transport of electronic data between computer systems, modules, and/or other electronic devices. When information is transferred, or provided, over a network (either hardwired, wireless, or a combination of hardwired and wireless) to a computer, the computer properly views the connection as a transmission medium. Computer system 700 will include one or more communication channels that are used to communicate with the network 708. Transmissions media include a network that can be used to carry data or desired program code means in the form of computer-executable instructions or in the form of data structures. Further, these computer-executable instructions can be accessed by a general-purpose or special-purpose computer. Combinations of the above should also be included within the scope of computer-readable media.

Upon reaching various computer system components, program code means in the form of computer-executable instructions or data structures can be transferred automatically from transmission media to computer storage media (or vice versa). For example, computer-executable instructions or data structures received over a network or data link can be buffered in RAM within a network interface module (e.g., a network interface card or "NIC") and then eventually transferred to computer system RAM and/or to less volatile computer storage media at a computer system. Thus, it should be understood that computer storage media can be included in computer system components that also (or even primarily) utilize transmission media.

Computer-executable (or computer-interpretable) instructions comprise, for example, instructions that cause a general-purpose computer, special-purpose computer, or special-purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the embodiments may be practiced in network computing environments with many types of computer system configurations, including personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The embodiments may also be practiced in distributed system environments where local and remote computer systems that are linked (either by hardwired data links, wireless data links, or by a combination of hardwired and wireless data links) through a network each perform tasks (e.g. cloud computing, cloud services and the like). In a distributed system environment, program modules may be located in both local and remote memory storage devices.

The present invention may be embodied in other specific forms without departing from its characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A system for facilitating image analysis, the system comprising:
    one or more processors; and
    one or more hardware storage devices that store instructions that are executable by the one or more processors to configure the system to:
        present a 3D representation of a set of 2D images within a 3D environment, each 2D image of the set of 2D images being associated with a respective selection mask, wherein the 3D representation represents pixels of the set of 2D images with corresponding voxels within the 3D environment;
        obtain user input directed to the 3D representation within the 3D environment, the user input selecting one or more voxels of the 3D representation; and
        based on the user input directed to the 3Drepresentation within the 3D environment, selectively modify one or more mask pixels of one or more of the respective selection masks, the one or more mask pixels being associated with one or more pixels of the set of 2D images that correspond to the one or more voxels of the 3D representation selected via the user input within the 3D environment, wherein a quantity of mask pixels that become selectively modified corresponds to a quantity of voxels selected via the user input directed to the 3D representation of the set of 2D images within the 3D environment.

2. The system of claim 1, wherein the set of 2D images comprises a set of grayscale images.

3. The system of claim 1, wherein the set of 2D images comprises a set of cross-sectional medical images.

4. The system of claim 1, wherein presenting the 3D representation of the set of 2D images within the 3D environment comprises causing display of the 3D representation on a display of an extended reality device.

5. The system of claim 4, wherein the user input is received via the extended reality device.

6. The system of claim 1, wherein, for each 2D image of the set of 2D images, the 2D image and the respective selection mask are composited as separate channels of a respective texture.

7. The system of claim 1, wherein selectively modifying the one or more mask pixels causes the one or more mask pixels to store a first value indicating selection for a calculation of an output metric.

8. The system of claim 7, wherein the instructions are executable by the one or more processors to further configure the system to generate the output metric using the one or more mask pixels.

9. The system of claim 8, wherein the instructions are executable by the one or more processors to further configure the system to display the output metric within an extended reality interface contemporaneous with (i) the 3D representation and (ii) a depiction of voxels that correspond to pixels of the set of 2D images that are associated with mask pixels that store the first value indicating selection for the calculation of the output metric.

10. The system of claim 8, wherein generating the output metric comprises:
    determining a set of mask pixels within the one or more of the respective selection masks that store the first value indicating selection for the calculation of the output metric; and
    calculating the output metric using the set of mask pixels.

11. The system of claim 10, wherein generating the output metric is performed utilizing a shader of a graphics processing unit.

12. The system of claim 10, wherein:
    determining the set of mask pixels within the one or more of the respective selection masks that store the first value indicating selection for the calculation of the output metric comprises, for each respective selection mask of the one or more of the respective selection masks, performing a reduction operation, wherein the reduction operation comprises, for each pixel region of a plurality of pixel regions of the respective selection mask, determining a respective sum of mask pixels within the pixel region, and
    the set of mask pixels is based upon each of the respective sums.

13. The system of claim 12, wherein the reduction operation comprises, for each respective selection mask of the one or more respective selection masks, outputting the respective sums of mask pixels as a reduced mask, each of the respective sums being represented as a corresponding pixel of the reduced mask, the reduced mask comprising a lower resolution than the respective selection mask, the reduced mask comprising higher-bit data than the respective selection mask.

14. The system of claim 12, wherein determining the set of mask pixels within the one or more of the respective selection masks that store the first value indicating selection for the calculation of the output metric further comprises performing one or more additional reduction operations based on output of the reduction operation or a preceding reduction operation, the one or more additional reduction operations comprising determining sums of regions of input pixels.

15. The system of claim 12, wherein the output metric comprises a volume.

16. The system of claim 1, wherein selectively modifying the one or more mask pixels causes the one or more mask pixels to store a second value indicating deselection of the one or more mask pixels or data associated therewith for a calculation of an output metric.

17. A method for facilitating image analysis, the method comprising:
presenting a 3D representation of a set of 2D images within a 3D environment, each 2D image of the set of 2D images being associated with a respective selection mask, wherein the 3D representation represents pixels of the set of 2D images with corresponding voxels within the 3D environment;
obtaining user input directed to the 3D representation within the 3D environment, the user input selecting one or more voxels of the 3D representation; and
based on the user input directed to the 3D representation within the 3D environment, selectively modifying one or more mask pixels of one or more of the respective selection masks, the one or more mask pixels being associated with one or more pixels of the set of 2D images that correspond to the one or more voxels of the 3D representation selected via the user input within the 3D environment, wherein a quantity of mask pixels of the one or more mask pixels that become selectively modified corresponds to a quantity of voxels of the one or more voxels selected via the user input directed to the 3D representation of the set of 2D images within the 3D environment.

18. The method of claim 17, wherein selectively modifying the one or more mask pixels causes the one or more mask pixels to store a first value indicating selection for a calculation of an output metric.

19. The method of claim 18, further comprising generating the output metric using the one or more mask pixels.

20. One or more hardware storage devices that store instructions that are executable by one or more processors of a system to configure the system to:
present a 3D representation of a set of 2D images within a 3D environment, each 2D image of the set of 2D images being associated with a respective selection mask, wherein the 3D representation represents pixels of the set of 2D images with corresponding voxels within the 3D environment;
obtain first user input directed to the 3D representation within the 3D environment, the first user input selecting one or more first voxels of the 3D representation;
based on the first user input directed to the 3D representation within the 3D environment, selectively modify one or more first mask pixels of one or more of the respective selection masks, the one or more first mask pixels being associated with one or more first pixels of the set of 2D images that correspond to the one or more first voxels of the 3D representation selected via the user input within the 3D environment, wherein selectively modifying the one or more first mask pixels causes the one or more first mask pixels to store a first value indicating selection for a calculation of an output metric;
obtain second user input directed to the 3D representation within the 3D environment, the second user input selecting one or more second voxels of the 3D representation; and
based on the second user input directed to the 3D representation within the 3D environment, selectively modify one or more second mask pixels of one or more of the respective selection masks, the one or more second mask pixels being associated with one or more second pixels of the set of 2D images that correspond to the one or more second voxels of the 3D representation selected via the second user input within the 3D environment, wherein selectively modifying the one or more second mask pixels causes the one or more second mask pixels to store a second value indicating deselection of the one or more second mask pixels or data associated therewith for the calculation of the output metric.

* * * * *